United States Patent [19]

Ogden

[11] Patent Number: 5,110,726
[45] Date of Patent: May 5, 1992

[54] IMMUNOASSAY FOR ANTIBODIES BINDING PLATELETS

[75] Inventor: Daryl M. Ogden, Harris, Tex.

[73] Assignee: Board of Regents, The University of Texas System, Austin, Tex.

[21] Appl. No.: 156,786

[22] Filed: Feb. 17, 1988

Related U.S. Application Data

[63] Continuation-in-part of Ser. No. 89,884, Aug. 27, 1987, Pat. No. 4,959,308.

[51] Int. Cl.$^5$ .................................... G01N 33/546
[52] U.S. Cl. ................................ 435/7.21; 424/11; 427/2; 435/2; 435/961; 435/962; 436/501; 436/534; 436/543; 436/824; 436/825
[58] Field of Search ............... 424/11; 435/2, 7, 7.21, 435/961, 962; 436/501, 506, 518, 530, 531, 533, 534, 543, 824, 825; 427/2

[56] References Cited

U.S. PATENT DOCUMENTS 4,717,654 1/1988 Savoca ............................ 436/501
4,810,632 3/1989 McMillan ...................... 436/507

FOREIGN PATENT DOCUMENTS 2027031 2/1980 United Kingdom .

OTHER PUBLICATIONS

Hudson et al., *Practical Immunology*, 2nd Ed., Blackwell Scientific Publications, Oxford, UK, 1980, p. 137.
Herbert et al., *Dictionary of Immunology*, 3rd Ed., Blackwell Scientific Publications, Oxford, UK, 1985, p. 101.
Kurata et al., *Vox Sang.*, 57, 199–204, 1989.
PCT International Search Report for PCT/US02953.
Petz, L. (1988), Am. J. Clin. Pathol., 90(1):114–5.
Ogden, et al., (1987), "An enzyme–linked immunosorbent assay for the detection of platelet antibodies using detergent–solubilized platelets immobilized on nitrocellulose discs", J. Immunological Methods, 105(1):63–70.
Nel, et al., (1980), *Br. J. Haematol*, 44:281–290.
Yesus, et al., (1984), *Amer. J. Clin. Pathol.*, 81:1.
LoBuglio, et al., (1983), *N. Engl. J. Med.*, 309:459–463.
Kickler, et al., (1983), *Blood*, 61:238–242.
Forster and Schmidt, (1983), *Klin. Wochenschr*, 61:165–167.
Kunicki, et al., (1979), *Mol. Immunol.*, 16:353–360.
Dutcher, et al., (1981), *Blood*, 58:1007–1011.
Newman, et al., (1981), *J. Cell Biol.*, 90:249–253.
Newman, et al., (1982), *Thromb. Res.*, 27:221–224.
Springer, et al., (1976), *Proc. Natl. Acad. Sci.*, 73:2481–2485.
Cook, et al., (1985), *Hum. Immunol.*, 14:234–244.
Baron, et al., (1975), *Biochim. Biophys. Acta*, 382:276–285.
Rosevear, et al., (1980), *Biochem.*, 19:4108–4115.
Hildreth, (1982), *Biochem. J.*, 207:363–366.
Cheng, et al., (1979), *J. Biol. Chem.*, 254:2165–2167.

(List continued on next page.)

Primary Examiner—David A. Saunders
Attorney, Agent, or Firm—Arnold, White & Durkee

[57] ABSTRACT

The present invention involves a method for producing a substrate useful in a system for the detection of antibodies directed against platelet antigens. This method comprises several steps. A platelet sample of interest is initially treated with an aqueous solution comprising a dialyzable nonionic detergent. This initial treatment is under conditions to solubilize platelet components and produce a platelet lysate. Such conditions may involve treatment of a platelet sample with an aqueous solution comprising nonionic detergent at a concentration between about 0.2% and about 0.5%. Platelet antigens are most preferably solubilized for about 30 min and at about 0° C. in an aqueous solution comprising about 1 mg dialyzable nonionic detergent per mg platelet protein.

The partially purified platelet antigens resulting from these manipulations are then preferably affixed to a solid matrix. The solid matrix preferably comprises nitrocellulose paper, polystyrene or latex but may be any solid matrix suitable for the abstraction from a biological sample and/or assay of antibodies binding to the affixed purified platelet antigens.

17 Claims, 3 Drawing Sheets

OTHER PUBLICATIONS

Beardsley, et al., (1984), *J. Clin. Invest.*, 74:1701–1707.
Heal, et al., (1987), *Blood*, 70:23–30.
McFarland, et al., (1987), *Blood*, 69:1425–1430.
Vos, et al., (1987), *Vox Sang*, 53:162–168.
Collins, et al., (1987), *Vox Sang*, 53:157–161.
Sintnicolaas, et al., (1987), *Brit. J. Haematol.*, 66:363–367.
Kelton, et al., (1987), *Am. J. Hemat.*, 25:299–310.
King, et al., *Blood*, 68:suppl. 1, abstr. 323.
Reid, et al., *Blood*, abstr. 338.
Steiner, et al., *Blood*, abstr. 350; abstr. 875.
Stricker, et al., *Blood*, abstr. 352.
MacPherson, et al., (1986), *Transfusion*, 26:467–470.
Velden, et al., (1986), *Brit. J. Haematol.*, 62:635–640.
Janson, et al., (1960), *Hum. Immunol.*, 15:251–262.
Stricker, et al., (1985), *N. Eng. J. Med.*, 313:1375–1380.
Dunstan, et al., (1985), *Brit. J. Haematol.*, 61:603–609.
Murphy, et al., (1985), *Brit. J. Haematol.*, 60:409–414.
Peters, et al., (1985), *Brit. J. Haematol.*, 60:117–127.
Yam, et al., (1984), *Brit. J. Haematol.*, 57:337–347.
Mason, et al., (1984), *Brit. J. Haematol.*, 56:529–534.
Boisvert, et al., (1983), *Am. J. Clin. Path*, 80:839–843.
Myers, et al., (1981), *Blood*, 58:444–450.
Tamerus, et al., (1983), *Blood*, 62:744–749.
Schiffer, et al., (1983), *Blood*, 61:311–317.
Palfree, et al., (1982), *J. Immunol. Meth.*, 52:395–408.
McMillan, et al., (1982), *Brit. J. Haematol.*, 51:297–304.
Lalezari, et al., (1982), *Blood*, 59:167–170.
Hecht, et al., (1982), *JAMA*, 248:2301–2303.
Waters, et al., (1981), *Brit. J. Haematol.*, 48:59–68.
Gould, et al., (1981), *Biochem.*, 20:6776–6781.
Gudino, et al., (1981), *Blood*, 57:32–37.
*Mayo Med. Labs. Comm.* (1983), 8:No. 12.
Schmidt, et al., (1980), *Blood*, 55:299–303.
Hagen, et al., (1979), *Eur. J. Biochem.*, 99:9–22.
Borne, et al., (1978), *Brit. J. Haematol.*, 39:195–207.
Wu, et al., (1976), *J. Clin. Invest.*, 58:432–438.
Dautigny, et al., (1973), *Biochim. Biophys. Acta*, 298:783–789.
McMillan, et al., (1971), *Blood*, 37:316–322.
Schiffer, *Seminar on antigens of Blood Cells and Body Fluids*, 189–208.
Sigma Chemical Company Catalog.
Ogden, et al., (1986), *Hum. Immunol.*, 17:154.
Triplett, (1978), *Platelet Function*, ASCP-Press ch 1:1–33.
Helenius, et al., (1979), *Methods in Enzymology*, LVI:734–749.
Parham, (1979), *J. Biol. Chem.*, 254:8709–8712.
Stubbs, et al., (1976), *Biochim. Biophys. Acta*, 425:46–56.
Lin, et al., (1979), *Biochim. Biophys. Acta*, 557:179–187.
Kahn, et al., (1981), *A Seminar on Immune-Related Cell Destruction*, 151–197.
Graddick, et al., (1987), *Diagnos. Clin. Immun.*, 5:82–85.
Millard, et al., (1987), *Blood*, 70:1495–1499.
Immuncor advertisement.
Bangs, Seradyn commercial literature.
Blumberg, et al., (1984), *Blood*, 63:448–450.
Kao, (1988), *Transfusion*, 28:14–17.
Hechemy, et al., (1984), *Laboratory Management*, Jun. 27–35.
Hechemy, et al., (1976), *J. Clin. Microbiol.*, 4:82–86.
Dixon, et al., (1975), *N. Eng. J. Med.*, 292:230–236.
Kiefel, et al., (1987), *Blood*, 70:1722–1726.
Nurden, et al., (1975), *Nature*, 255:720–722.

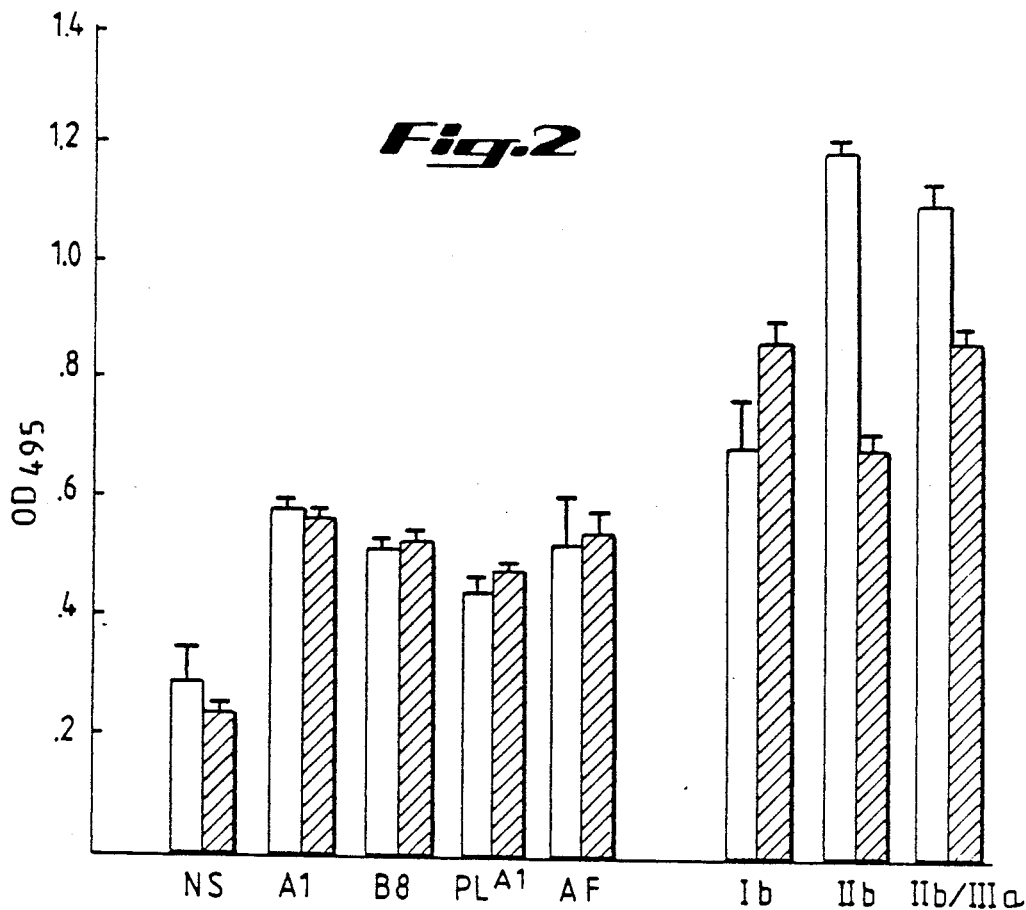
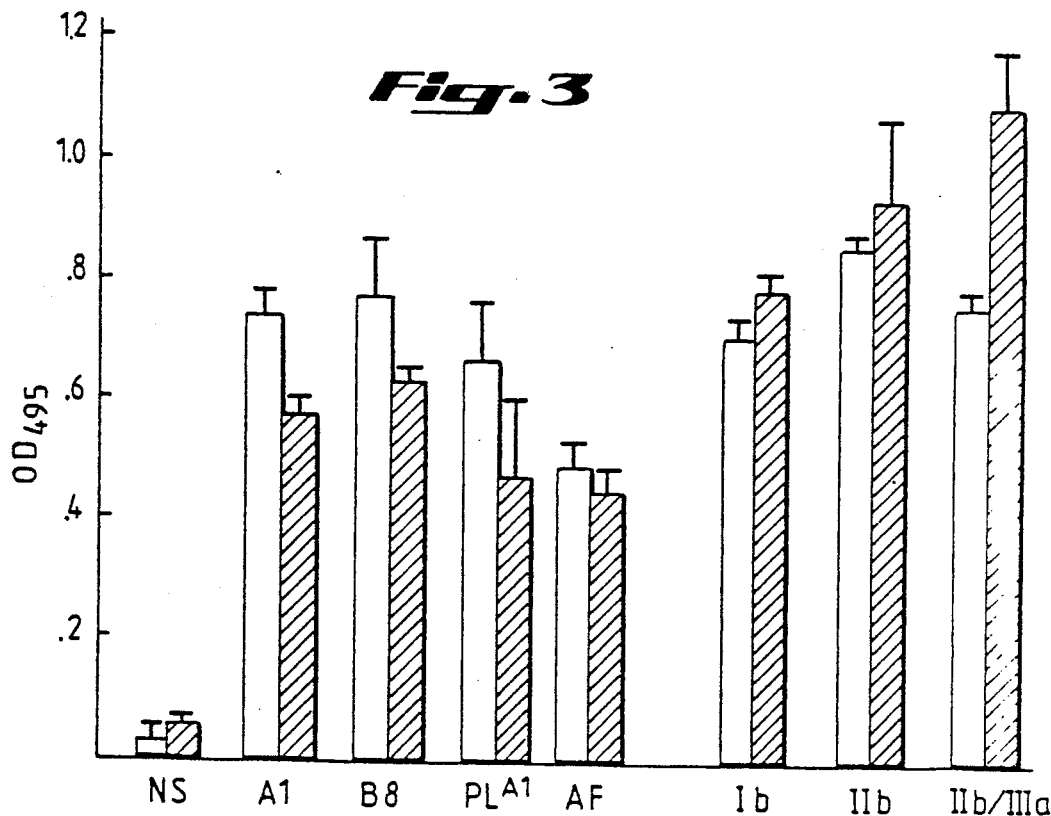

IMMUNOASSAY FOR ANTIBODIES BINDING PLATELETS

This is a continuation-in-part of U.S. application Ser. No. 089,884, filed Aug. 27, 1987, now U.S. Pat. No. 4,959,308, entitled IMMUNOASSAY FOR ANTIBODIES BINDING PLATELETS by Daryl M. Ogden.

The present invention relates to a process for determination of the presence of antibodies directed against platelets. This process involves the preparation and use of solubilized platelet antigens freed of substances nonimmunospecifically binding to human IgG.

Platelet transfusion is an important hemotherapeutic supportive measure, particularly for patients undergoing bone marrow transplantation or cytoreductive chemotherapy for hematologic malignancies. Alloimmunization to antigens presented on the transfused cells becomes problematic in as many a 70% of the patients, making them refractory to further random donor platelet transfusions. Although they may initially respond to single donor, HLA-matched platelets, more recent studies have suggested that HLA matching may not reliably predict the outcome of such transfusions. This is due at least in part to the varied number of platelet membrane components that can serve as immunologic targets, some of which are still undefined. Two classes of defined platelet surface antigens exist: those also found on other cells (blood group, histocompatibility, T, and Tn antigens) and those unique to platelets.

The ABO blood group antigens (BGA) were detected on platelets more than thirty years ago. It has since been shown that these antigens are adsorbed to the surface of the platelet rather than being an intrinsic part of the membrane structure. The amount of BGA substance on platelets is proportional to the amount in the plasma. In addition, these platelet-BGA substances possess different biochemical characteristics than BGA substances present on erythrocytes. As such, transfusion with ABO-incompatible platelets causes only an initial reduction in platelet recovery, the remaining platelets surviving normally. BGA have been implicated as the target antigens responsible for transfusion failures of ABO-mismatched, HLA-matched platelets in two leukemia patients. Platelets probably do not carry any of the other BGA.

The cryptic Tn antigen has alpha-N-acetyl-D-galactosamine residues as the immunodominant group, is responsible for polyagglutination of certain red cells by antibody and is also present on platelets. Abnormal exposure of the Tn antigen may result from a deficiency of specific galactosyl transferase activity (T-transferase) and is often associated with thrombocytopenia.

The T (Thomsen-Friedenreich) antigen is a similarly cryptic beta-D-galactosyl residue which can be exposed by treatment with neuraminidase.

Class I antigens of the major histocompatibility complex are also thought to be absorbed to the surface of the platelet. In fact, platelets carry approximately 73% of the total HLA-A and -B content of the blood. Studies have clearly shown that these antigens are the most immunogenic of the various antigens expressed on the platelet surface. At the same time, it is well recognized that there can be differing expression of HLA antigens not only on different cell types but also in quantitative expression on platelets from the same individual.

The existence of distinct platelet-specific antigens was first recognized more than 30 years ago. Seven antigenic systems containing eleven different antigens have now been described, all being products of autosomal dominant genes. The $PL^A$ (Zw), $PL^E$, and KO systems are diallelic, while $BAK^a$, $LEK^a$, and DUZO have only single alleles detected thus far.

The above antigens are really epitopes on defined membrane glycoproteins (GP), which in turn possess receptor characteristics for specific platelet biochemical functions. These biochemical functions include binding of thrombin by GPIb, fibrinogen by the GPIIb/IIIa complex, and serving as the thrombin substrate by GPV.

Alloimmunization to platelets can be demonstrated using a variety of in vitro laboratory methods, including radiometric tracers, immunofluorescence, antiglobulin or complement consumption, platelet activation, and enzyme-linked immunoassays. The development of such assays has been pursued with a variety of successes, especially as relates to a crossmatching procedure.

Complement activation assays are attractive procedures in theory. In practice, however, these have poor sensitivity. Since antibody-coated platelets are removed from the circulation by macrophages, platelet adherence and phagocytosis are plausible alternatives to complement fixation tests, but the procedures so far designed are cumbersome and poorly reproducible. Although the methods utilizing the antiglobulin principle are relatively simple, sensitive, and quantitative, they all share an intrinsic complicating problem. Due to the platelet's ability to adsorb plasma components, including IgG (Triplett (1978) in Platelet Function: Laboratory Evaluation and Clinical Applications (D. Triplett, ed.) pp. 1-34, ASCP Press, Chicago), most of these assays have high background values obtained by measuring both the immune-bound and nonspecifically-bound IgG. These high background values make suspect measurements of platelet-associated IgG (PAIgG) other than those substantially above normal values, the range of which has been reported to be from 1.7 fg to 15.5 ng IgG ($7 \times 10^3$ to $1.6 \times 10^7$ molecules IgG) per platelet (Dixon et al. (1975) N. Engl. J. Med., 292:230-236; Nel et al. (1980) Br. J. Haematol, 44:281-290; Yesus et al. (1984) Amer. J. Clin. Pathol., 81:1). LoBuglio et al. have introduced an $^{125}$I-labelled anti-IgG technique to lower these values to about $169 \pm 79$ IgG molecules per platelet (LoBuglio et al. (1983) N. Engl. J. Med., 309:459-463).

An object of this invention is the development of an effective in vitro platelet antibody detection assay or crossmatching procedure to identify compatible platelet donors, particularly for multitransfused patients refractory to platelet transfusion. Such a procedure preferably involves preparation of a bank of stored donor platelet samples against which a patient's serum may be screened for the presence and quantity of antibody. Methods designed to store such platelet aliquots for long term use in laboratory assays have been reported.

Kikler et al. took segments from pheresis bags to isolate donor platelets and use in a radiolabeled antiglobulin test (Kikler et al. (1983) Blood, 61:238-242). However, since pheresed platelets can be stored no longer than 120 hours, the test is limited to donors accruing within such a time period. Forster et al. isolated platelets from EDTA-anticoagulated blood samples and fixed them with 1% paraformaldehyde prior to their use in a microELISA assay (Forster et al. (1983) Klin. Wochenscher, 61:165-167). In contrast, platelets preserved either by desiccation (stored for up to thirty days) or in normal saline containing 0.01% sodium azide (stored for up to 417 days) gave reproducible results that correlated well with results obtained using fresh platelets.

Therefore, an important aspect of the present invention is the preparation of suitable donor-specific platelet "reagents" that are stable over long periods of storage, are compatible with a reliable and efficient assay, and result in minimal non-specific reactivity. Such platelet reagents may, as described in the present invention, be prepared by certain detergent solubilization of the platelet membranes, followed by the coupling of solubilized membrane components to an inert matrix for immunoassay. It is paramount, however, that the native biological activities of such solubilized components be preserved and that the detergent not interfere with subsequent biochemical or immunological assays.

Non-ionic detergents vary in their effectiveness to solubilize biological membranes and to maintain native activities of the components. The inability of these detergents to be completely removed from the reaction media because of their low critical micell concentrations, large micell sizes, and high affinity for membrane proteins limits their applicability to various test systems (Helenius et al. (1979) in Methods in Enzymology (S. Fleischer and L. Packer, eds.) Vol. LVI, p. 734-749. Academic Press, London and New York).

Both platelet-specific glycoproteins (GP) and HLA antigens have been solubilized with a variety of non-ionic detergents in efforts to study the specific roles of membrane glycoproteins in platelet immune function. Kunicki et al. localized the $Pl^{A1}$ alloantigen to the GPIIIa component using Nonidet P40 (Kunicki et al. (1979) Mol. Immunol., 16:353-360). Triton X-100 has been widely used to characterize the structure and composition of platelet surface components (Dutcher et al. (1981) Blood, 57:395-398), to detect monoclonal antibodies (moAb) to platelet membrane proteins (Newman et al. (1982) J. Cell Biol., 90:249-253), and to study platelet-associated IgG in alloimmunized patients (Yohannes et al. (1983), Amer. J. Clin. Pathol., 81:81-84). Triton X-114 (Newman et al. (1982) Thromb Res., 27:221-224) has been applied for the selective extraction of integral membrane proteins, whereas both Brijj-99 Springer et al. (1976) Proc. Natl. Acad. Sci. USA, 73:2481-2485) and Nonidet P40 (Parm (1979) J. Biol. Chem., 254:8709-8712; Cook et al. (1985) Hum. Immunol., 14:234-244) have been used to probe the structure of HLA antigens on the platelet surface.

The research of Baron and Thompson (Baron et al. (1975) Biochem. Biophys. Acta., 382-276-285) led to the introduction of the non-ionic alkyl-beta-D-glucoside detergents which have since been found to surpass cationic, zwitterionic and other non-ionic detergents in their abilities to solubilize, retain native functions of the components, and be completely removed from the lysate (Stubbs et al. (1976) Biochem. Biophys. Acta, 426-46-56; Lin et al. (1979) Biochem. Biophys. Acta, 557:179-187; Rosevear et al. (1980) Biochem., 19:4108-4115). Hildreth compared the capacity of several of these alkyl glucosides for solubilizing transformed cell lines, and found them as effective as or superior to other commonly used detergents in releasing antigenically active class I histocompatibility antigens (Hildreth (1982) Biochem. J., 207:363-366).

Further, it has been shown that the immunoreactivity of solubilized membranes can be preserved following their chemical coupling to a variety of solid matrices, including cyanogen bromide-activated filter paper discs, nitrocellulose paper and polystyrene microtiter plates.

As stated above, most platelet antibody assays currently being used are designed to detect PAIgG with a marker-labeled anti-IgG, making it impossible to differentiate immune from nonimmune immunoglobulin attached to the platelet surface. In the past, investigators have attempted to block or dissociate the non-specifically bound IgG with various detergents, albumin solutions or platelet pretreatments. It is apparent, however, that these standardly used blocking methods do not altogether inhibit nonimmunospecific IgG binding to the platelet surface. This may indicate that the affinity of at least some of the nonimmune IgG for the platelet membrane is greater than the affinity described for general non-specific protein-protein binding. This phenomenon of nonimmunospecific but strong binding may be the result of receptor-like proteins for IgG on the surface of the platelet.

Cheng et al. affinity isolated and characterized a specific platelet membrane glycoprotein which interacted the $F_c$-fragment of IgG (Cheng et al. (1979) J. Biol. Chem., 254:2165-2167). Beardsley et al. reported the binding of non-specific IgG to a 200 kilodalton glycoprotein separated by SDS-PAGE from detergent solubilized platelets (Beardsley et al. (1984) J. Clin. Invest., 74:1701-1707). It is generally accepted that there is an isolable platelet membrane component with a high affinity for normal, nonimmune IgG.

The present invention details a method by which random donor platelets were solubilized with the non-ionic detergent decanoyl-N-methylglucamide (Mega 10), dialyzed to remove excess detergent, and partially purified using affinity chromatography with agarose-bound IgG. The detergent lysate was immobilized onto nitrocellulose discs which were then incorporated into an enzyme-linked immunoassay to detect the presence of immunologically active platelet membrane components and clinically significant antibodies in the sera of multitransfused platelet recipients.

In addition, the invention provides for a rapid latex agglutination assay using the purified platelet antigens. And, in an additional embodiment, the invention provides a method whereby one may discriminate antisera having antibodies against HLA antigens from antisera having antibodies specific for integral platelet membrane antigens.

BRIEF DESCRIPTION OF THE DRAWINGS

FIG. 2 shows the detection and stability of nitrocellulose-bound PLy. Nitrocellulose discs were dotted with 20 ug of PLy as described herein, and were then incubated with 1:10 dilutions of: (NS) normal sera, ($Pl^{A1}$) anti-$Pl^{A1}$, (AF) alloimmune serum, (A1) anti- HLA-A1 or (B8) anti-HLA-B8, or 500 ng of monoclonal antibody to the platelet glycoproteins GPIb, GPIIb, or GPIIb/IIIa. A 1% bovine serum albumin solution (BSA) was used as a control. All dilutions were made in 10 mM-TBS, pH 7.4. Bound antibody was detected with alkaline phosphatase-conjugated anti-IgG using freshly prepared discs (open bars) and discs stored for 100 days (hatched bars).

FIG. 3 shows detection and stability of nitrocellulose-bound PAb. Nitrocellulose discs were dotted with 20 ug of PAb as described herein, and were then incubated with 1:10 dilutions of: (NS) normal sera, (P1$^{A1}$) anti-P1$^{A1}$, (AF) alloimmune serum, (A1) anti-HLA-A1 or (B8) anti-HLA-B8, or 500 ng of monoclonal antibody to the platelet glycoproteins GPIb, GPIIb, or GPIIb/IIIa. A 1% bovine serum albumin solution (BSA) was used as a control. All dilutions were made in 10 mM-TBS, pH 7.4. Bound antibody was detected with alkaline phosphatase-conjugated anti-IgG using freshly prepared discs (open bars) and discs stored for 100 days (hatched bars).

SUMMARY OF THE INVENTION

Figure 1:
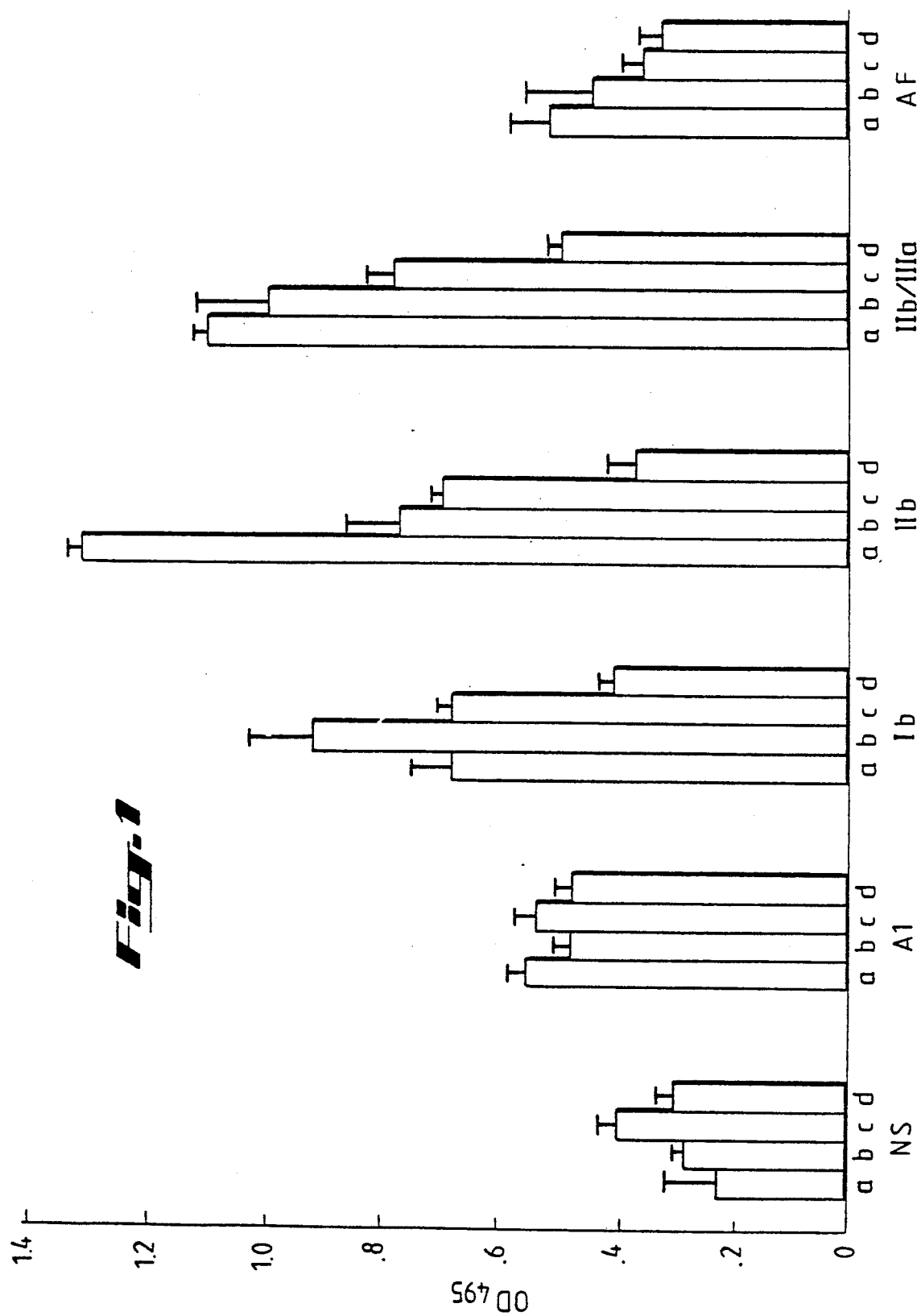
FIG. 1 shows the ability of antibody to detect various quantities of nitrocellulose-bound platelet detergent lysate. Platelet detergent lysate (PLy) was prepared as described herein and (a) 20 ug, (b) 10 ug, (c) 5 ug, or (d) 1.0 ug was applied to nitrocellulose discs. Normal serum (NS), anti-HLA-A1 (A1), or alloimmune serum (AF), diluted 1:10 in TBS, or 500 ng of moAb to GPIb, GpIIb, or GPIIb/IIIa were incubated with the discs, and bound antibody was subsequently detected with alkaline phosphatase-coupled anti-IgG.

The present invention involves a method for producing a substrate useful in a system for the detection of antibodies directed against platelet antigens. This method comprises several steps. A platelet sample of interest is initially treated with an aqueous solution comprising a dialyzable nonionic detergent. This initial treatment is under conditions to solubilize platelet components and produce a platelet lysate. For an assay to detect the presence of antibody to platelets, the "platelet sample" would be Pab prepared from a pool of aliquots from 30-40 units of platelet-rich plasma. For a crossmatch assay, "platelet sample" would be Pab prepared from an individual unit of pheresed platelets. Such conditions may involve treatment of a platelet sample with an aqueous solution comprising nonionic detergent at a concentration between about 0.2% and about 0.5%. Platelet antigens are most preferably solubilized for about 30 min. and at about 0° C. in an aqueous solution comprising about 1 mg dialyzable nonionic detergent per mg platelet protein.

Insoluble material and excess detergent are preferably next separated from the lysate to produce a solution comprising solubilized platelet antigens. Insoluble material is preferably removed by centrifugation of the lysate and detergent is preferably removed by dialysis.

Substances nonimmunospecifically binding to human IgG are then removed from said solution to produce partially purified platelet antigens. The removal of these substances nonimmunospecifically binding to human IgG preferably involves contacting the solution with human IgG attached to a solid matrix. For example, the platelet lysate, freed of insoluble material and excess detergent may be chromatographically run through a column of IgG-agarose. The lysate may then be further purified, for example, by affinity chromatography to remove HLA antigens, if so desired.

The partially purified platelet antigens resulting from these manipulations are then preferably affixed to a solid matrix. The solid matrix preferably comprises nitrocellulose paper, polystyrene or latex but may be any solid matrix suitable for the abstraction from a biological sample and/or assay of antibodies binding to the affixed purified platelet antigens. In one preferred embodiment, the solid matrix comprises a particulate matrix, for example, latex beads.

When a particulate matrix is used, it will usually be suspended in a suitable solution (the continuous phase). For reasons described herein, it will often be desirable to have only a fraction of the antigens affixed to the matrix, the remainder remaining dissolved in the continuous phase or solution. In a preferred embodiment, the ratio (as measured by weight) of antigens remaining dissolved in the suspending solution or continuous phase to the affixed antigens ranges from about 1.6 to about 6.0.

Insofar as the present invention concerns a method for detecting antibodies directed against platelets in a biological sample, the method comprises, in addition to the preparation of the substrate described above, the steps of contacting said solid matrix with a solution comprising the biological sample and measuring the amount of antibody bound to the solid matrix.

When the biological sample of interest is a platelet source and the identification of a platelet source immunologically compatible with a prospective platelet recipient is an object of the present invention, the method, in addition to producing a substrate as described above with the platelet sample being from the platelet source, involves additional steps. As a negative control, a sample is obtained from a pool of previously untransfused male individuals having an AB positive blood type. Such previously untransfused males should not have antibodies against platelet antigens. An antibody-containing sample is obtained from a prospective platelet recipient, in need or potentially in need of platelet transfusion.

A first portion of said affixed partially purified platelet antigens (substrate) is contacted with an antibody-containing sample from the prospective platelet recipient under conditions facilitating binding of antibody specific for platelet antigens to the affixed partially purified platelet antigens. A second portion of said affixed partially purified platelet antigens is contacted with an antibody-containing sample from the previously untransfused male having an AB positive blood type under the same conditions. A first level of antibody bound to the first portion of the affixed partially purified platelet antigen and a second level of antibody bound to the second portion of the affixed partially purified platelet antigens are then determined. This determination may be by any of numerous means known to those skilled in the relevant arts, includes Enzyme Linked Immunoadsorbent Assays (ELISA) and visual or spectrophotometric determinations of turbidity resulting from immunocomplex formation or agglutination, particularly the latter in the case where the solid matrix is latex in bead form.

The first level of bound antibody is then compared to the second level of bound antibody. A platelet source immunologically compatible (not having substantial levels of antibodies directed against platelet antigens of the platelet source) with said prospective platelet recipient is identified when said first level is not substantially greater than said second level. The processes of the present invention are particularly useful to cross-match immunologically compatible platelet sources with patients previously refractory to circulating platelet increases after platelet transfusion.

The methods of the present invention also allow detection of antibodies directed against certain platelet antigens now believed to represent non-integral platelet membrane proteins, for example, HLA antigens, more particularly, HLA-A and HLA-B antigens. In general, this method involves elution of antigens prior to treatment of the platelets with non-ionic detergent. Chloroquine is a preferred eluting reagent.

Preferred detergents for use in the practice of the present invention are alkyl-N-methylglucamides or alkylglycosides, more preferably the former. Among the more preferable alkyl-N-methylglucamides are decanoyl-N-methylglucamide, nonanoyl-N-methylglucamide, octanoyl-N-methylglucamide and heptanoyl-N-methylglucamide. The most preferred detergent of the present invention is decanoyl-N-methylglucamide. Usable alkylglycosides include n-decyl beta-D-glucopyranoside, n-dodecyl beta-D-glucopyranoside, n-dodecyl beta-D-maltoside, n-heptyl beta-D-glucopyranoside, n-hexyl beta-D-glucopyranoside, n-octyl beta-D-glucopyranoside, n-nonyl beta-D-glucopyranoside and n-octyl-alpha-D-glucopyranoside.

DESCRIPTION OF THE PREFERRED EMBODIMENT

These specifics are presented to illustrate preferred embodiments and utilities of the present invention and are not meant to limit the present invention unless otherwise specifically stated in the claims appended hereto.

The following reagents were purchased from Sigma Chemical Co., St. Louis, Mo.: Decanoyl-N-methylglucamide (Mega-10); Polyvinylpyrolidone; gamma globulin-free bovine serum albumin (BSA); Pooled human male AB serum; poly-L-Lysine; Agarose-bound human IgG; 3-amino-9-ethylcarbazole; Alkaline phosphatase conjugated F(ab)$_2$ fragments of sheep anti-mouse IgG and goat anti-human IgG; p-nitrophenylphosphate substrate and diethanolamine. Bio-Rad dye-reagent protein assay was obtained from BioRad Laboratories, Richmond, Calif. Nitrocellulose paper (0.45 um) was purchased from Schleicher and Schuell, Inc., Keene, N.H. Avidin-Biotin test reagents were supplied by Vectastain Labs, Inc., Burlingame, Calif. Tissue typing trays were purchased from One Lambda, Los Angeles, Calif., and Geometric Data, Wayne, Pa. Anti-Pl[A1] alloantiserum was a gift from Dr. R. Aster (Blood Center of Southeast Wisconsin, Milwaukee, Wis.). Mouse monoclonal antibodies (moAb) from ascites fluid were generously provided by Dr. R. P. McEver (University of Texas Health Science Center, San Antonio, Tex.). Sera from alloimmunized individuals (AF,DP) were collected from the U.T.M.D. Anderson Hospital Blood Bank. All other chemical were of analytical grade.

Platelet-rich plasma was prepared by differential centrifugation of Group O, Rh-positive blood anticoagulated with citrate phosphate dextrose adenine. Platelets were isolated according to the procedure described by Schiffer and Young (1983). Purity was assessed by light microscopy and the preparation shown to contain less than one red blood cell or leukocyte per 1000 platelets. Platelet counts were electronically performed using the Coulter S-Plus cell counter. Mononuclear cells were isolated using Ficoll-Hypaque density gradients as described by Boyum (1968).

Platelet preparations were centrifuged, the supernates discarded, and the platelet buttons weighed. A 10% stock solution of detergent was made in methanol and diluted with 50 mM-Tris-HCl, pH 8.0, containing 0.15M-NaCl (TBS) and 1 mM-phenylmethanesulfonyl fluoride, to make a 0.5% working solution. The platelets were solubilized using a detergent/protein ratio of 1:12 for 30 min on ice with occasional shaking. This lysate (PLy) was centrifuged at 50,000×G for 1 hr at 4° C., and the supernate dialyzed overnight at 4° C. against 10 mM-TBS, pH 8.0, 0.02% sodium azide. Protein concentrations were determined colorimetrically. Bovine serum albumin was used as the standard. Aliquots of PLy were frozen at −70°C.

Five hundred microliters of agarose-bound IgG (AgIgG) were centrifuged for 2 min at 3000×g and the supernate removed. Ply was diluted to 1.5 mg/ml with TBS and 1.0 ml of this was added to the AgIgG and placed on a rotating platform for 30 min at room temperature. The mixture was centrifuged as above, the supernate removed, and added to 500 ul of packed, fresh AgIgG. The incubation was repeated and the absorbed supernate (PAb), free of non-specific IgG-binding matter, removed after centrifugation. Protein determinations were made of the supernates following each absorption. Aliquots of PAb were stored at −70°C.

Bovine serum albumin (BSA), 1.0 mg/ml in TBS, was absorbed using the above conditions to determine the specificity of protein adherence to AgIgG.

Nitrocellulose discs (NC) were prepared using a standard 6-mm hole punch. Before use, the discs were hydrated with distilled water for 5 min and then air dried. PLy/PAb of various concentrations in volumes of 10-15 ul were dotted onto NC and allowed to air dry. NC discs were stored in airtight containers at 4° C. until use. All subsequent steps were performed at room temperature unless otherwise stated.

For the ELISA, one NC was placed in a 12×75 mm glass tube and 100 ul (microliter) of 1% polyvinyl pyrrolidone-1% bovine serum albumin solution were added to block excess binding sites. After 30 min incubation, the blocking solution was aspirated and 100 ul of normal control serum, 1% BSA, or the appropriate test serum (diluted in 10 mM-TBS, pH 7.5, 1 mM CaCl$_2$) were added to duplicate tubes. The discs were incubated in a 37° C. water bath for 1 hr, followed by three-10 min washes with 10 mM-TBS, 0.01% goat serum. Two hundred microliters of the enzyme-conjugated anti-IgG (diluted 1:750 in TBS) were added, and the reaction mixture was incubated for 1 hr with continuous shaking. The enzyme conjugate was aspirated and the discs were washed three times with TBS. Alkaline phosphatase activity was detected at 37° C. following the addition of 200 ul p-nitrophenylphosphate substrate, 1.0 mg/ml in diethanolamine buffer, pH 9.8, according to Schiffer and Young (Schiffer et al. (1983) Blood, 61:311-317).

Optical density readings at 405 nm were made using a Dynatech micro-ELISA reader.

One microliter of PLy (1.0 mg/ml in 10 mM-TBS) was added to each well of a commercially prepared, 60-well microtiter tray containing 1.0 ul of HLA-A,B, or C locus-specific antiserum, and the contents were incubated for 30 min at room temperature. Autologous or random lymphocytes, isolated as described above, were added to each well and the procedure for a standard microcytotoxicity assay followed (Mittal et al. (1968) Transplantation, 6:913–916).

Platelets were isolated and pooled from the pilot segments of 40 platelet rich plasma units. An aliquot of this pool was bound to glass slides with poly-L-lysine using a modified method of Trinidad et al. (Trinidad et al. (1983) in Abstracts of the Ninth Annual Meeting of the Amer. Assoc. Clin. Histocompatibility Testing, Chicago, Ill., p. 50). All steps were performed at room temperature. Ten microliters of antiserum (diluted 1:10 with TBS) which had been previously absorbed for 30 min with either 5 ul PLy (1.0 mg/ml) or with TBS were added to the bound platelets. After washing with TBS, 10 ul of biotinylated anti-IgG were added for 30 min. The slides were washed and 10 ul of an avidin-biotinylated lactoperoxidase -solution were added for 45 min. Enzyme activity was detected microscopically after a 5 min incubation with 3-amino-9-ethylcarbazole (0.5 mM in 100 mM-sodium acetate buffer, pH 5.2).

Solubilization of 1.0 g (approximately $2.3 \times 10^{10}$) platelets typically yielded 26.0 ±3 mg protein. The same yield was obtained when the detergent/protein ratio was decreased twofold. Some insoluble material was seen after ultracentrifugation, and none was observed following dialysis. Thawing and centrifugation of frozen aliquots never reduced the protein concentration of any extract tested.

Table 1 details the results of multiple absorption of two different PLy preparations and the BSA control solution. A consistent loss of protein was noted with two absorptions of the PLy with AgIgG. A third treatment with fresh AgIgG, however, did not further decrease the protein concentration. The total loss of protein with this procedure for the two Ply preparations was 32% and 25%. All subsequent absorptions of PLy were therefore carried out at the ratio of 1.5 mg PLy/1.0 ml of AgIgG. The average loss of protein using eight different PLy preparations was 29.4±4%. This absorption was a specific phenomenon, as demonstrated by the recovery (107%) of BSA following identical treatment with AgIgG.

TABLE 1

RECOVERY OF PROTEIN FOLLOWING ABSORPTION OF PLATELET LYSATE WITH AGAROSE-IgG

| Exp. | mg PLy Added to Agarose-IgG | mg (%)* PAb Recovered Following Absorbtion | | |
|---|---|---|---|---|
| | | #1 | #2 | #3 |
| I | 1.50 | 1.16 (78) | 1.03 (69) | 1.02 (68) |
| II | 1.50 | 1.26 (84) | 1.10 (73) | 1.13 (75) |
| BSA | 1.00 | 1.07 (107) | | |

*percent of starting material

The ability of PLy to inhibit specific, complement-mediated lymphocytotoxic antibody is shown in Table 2.

TABLE 2

INHIBITION OF ANTIBODY-MEDIATED CLASS I LYMPHOCYTOTOXICITY WITH PLy AND PAb

| DONOR | HLA LOCUS | ANTIGEN PRESENTED ON DONOR'S LYMPHOCYTES | INHIBITION BY DONOR'S PLy/PAb* |
|---|---|---|---|
| I | A | 11 | + |
| | | 9 | + |
| | | 24 | + |
| | B | 40 | + |
| | | 5 | + |
| | | 51 | + |
| II | A | 3 | N |
| | | 29 | + |
| | B | 18 | + |
| | | 12 | + |
| | | 45 | + |
| III | A | 9 | + |
| | | 24 | + |
| | B | 5 | + |
| | | 51 | + |
| | | 12 | N |
| | | 44 | N |

*+ = >95% inhibition
N = <5% inhibition

Except in the cases of anti-A3 (donor II) and anti-B44(12) (donor III), detergent extracts of donors' platelets completely inhibited cytotoxicity of antisera directed against HLA antigens on autologous lymphocytes and against identical antigens on allogeneic lymphocytes. PLY never inhibited the cytotoxic reactions of antiserum directed against non-self antigens, although a slight decrease (<20%) in reactivity of antisera to known crossreactive antigens was occasionally noted. It is important to note that whole platelets from Donor 2 inhibited cytotoxic activity of all specific antisera except anti-HLA-A when tested in the same assay.

PLy and PAb had the capacity to completely absorb anti-Pl$^{41}$ activity as measured by using a sensitive avidin-biotin immunoperoxidase assay. Anti-Pl$^{41}$ absorbed with the PLy or PAb failed to result in any which was bound immunoperoxidase activity. The same lack of peroxidase activity was obtained when serum collected from an individual alloimmunized to platelets as a result of multiple transfusions or when HLA-specific alloantiserum was absorbed.

There was a complete loss of enzyme activity following its absorption with PLy. However, little reduction in the intensity or pattern of staining of the platelets was noted when compared to the control. This was because PAb had that membrane component(s) responsible for the binding of nonimmune IgG previously absorbed with the agarose-bound Ig.

In order to determine the optimal amount of solubilized material to bind to the NC discs for the ELISA, decreasing quantities of PLy were applied to the discs and incubated with normal serum or antibody to the various antigens shown in FIG. 1. The major platelet glycoproteins GPIa, GPIb. GPIIb/IIIa complex, HLA-A1, and the allodeterminate(s) defined by serum AF were all detectable with as little as 1.0 ug of PLy per NC disc. With this quantity of PLy, however, it was not possible to discriminate between the normal serum control and AF, the latter showing only a 6% increase in average reactivity. Since 20 ug/disc gave the highest reactivity in general, this amount was used in all subsequent experiments.

The effect of absorption of Ply with AgIgG on the binding of normal serum in shown in Table 3.

TABLE 3

EFFECT OF ABSORBTION OF PLy WITH AGAROSE-IgG ON THE BINDING OF NORMAL SERUM

| Sample | Avg. OD$_{495}$ ($\pm$ s.d.) | | Percent Decrease |
| --- | --- | --- | --- |
| | PLy | PAb | |
| NS-1 | .22 (.02) | .03 (.02) | 87 |
| NS-2 | .25 (.03) | .09 (.02) | 64 |
| NS-3 | .29 (.01) | .10 (.01) | 64 |
| NS-4 | .14 (.02) | .03 (.01) | 80 |
| NS-5 | .26 (.01) | .04 (.01) | 87 |
| PHS | .34 (.02) | .07 (.01) | 80 |
| average | .25 (.02) | .06 (.01) | 77 (11) |

Values have been corrected for enzyme substrate binding to discs. OD$_{495}$ + .20 $\pm$ .02

Sera from five individuals, as well as from a commercially obtained pool of human serum were incubated with discs dotted with either PLy or PAb, and probed with enzyme conjugated anti-human IgG. The level of non-specific binding of the secondary reagents to the nitrocellulose was determined by substituting TBS for the primary antibody. An average 77% (range: 63–90) decrease in detectable IgG was noted in the PAb values compared to PLy. Secondary reagent binding contributed 0.20 $\pm$0.02 optical density (OD) units to each reaction, and was therefore substracted from all subsequent readings.

The ELISA was performed using both freshly prepared discs and those stored at 4° C. This was done to establish the stability of NC-bound PLy. Using PLy discs, no loss after a 100 day storage period of HLA-A1, $-$B8, PL$^{A1}$, or GPIb activity was seen. A storage-dependent decrease of about 35% and 15% was evident in the GPIIb and GPIIb/IIIa reactivity, respectively (FIG. 2). These latter values were still, however, 2.5-fold greater than the normal serum control, and almost five-fold higher than the BSA control. The same antigens were as equally stable in the NC-bound PAb following a 100 day storage period (FIG. 3), although an 18% and 15% decrease in the HLA-A1 and $-$B8 activity, respectively, was noted. These values were still significantly above the normal serum controls.

The sensitivity of this ELISA system was also investigated by incubating decreasing quantities of antibody with a consistent amount of immobilized Ply/PAb (20 ug/disc). As seen in Table 4 using PLy-bound discs, specific antibody can be detected even at a dilution of 1:100, with OD values 1.7 and 1.5-times higher than the normal serum control for anti-PLA1 and serum AF, respectively.

TABLE 4

ABILITY OF NITROCELLULOSE-BOUND PLy AND PAb TO DETECT DECREASING QUANTITIES OF ALLOANTIBODY

| Sample | Dilution$^{-1}$ | Avg. OD$_{495}$ ($\pm$ s.d.)* | |
| --- | --- | --- | --- |
| | | PLy | PAb |
| NS | 10 | .22 (.04) | .02 (.01) |
| | 50 | .40 (.06) | .17 (.01) |
| | 100 | .38 (.07) | .10 (.03) |
| PL$^{A1}$ | 10 | .45 (.01) | .40 (.01) |
| | 50 | .64 (.04) | .59 (.02) |
| | 100 | .62 (.020 | .40 (.02) |
| HLA-A1 | 10 | .62 (.01) | .75 (.02) |
| | 50 | .46 (.07) | .43 (.05) |
| | 100 | .31 (.01) | .43 (.01) |
| AF | 10 | .53 (.03) | .27 (.02) |
| | 50 | .65 (.06) | .47 (.03) |
| | 100 | .58 (.05) | .45 (.06) |

*Values have been corrected for substrate binding to discs, OD$_{495}$ = .20 $\pm$ .02.

The anti-HLA-A1, however, failed to show an increase over the control at both 1:50 and 1:100 dilutions. Two- to three-fold increases were seen for all three antisera at 1:10.

These results may be contrasted with those obtained with the same assay using NC-bound PAb, also shown in Table 4. While enzyme activities were four-fold higher than PLy values in all antisera at a 1:100 dilution, most noticeable were the values obtained at 1:10 dilutions. These were 20 to 35 times higher than the control serum values. Normal serum binding at a 1:10 dilution was greatly reduced following absorption of the PLy, to one-tenth (0.02) the value observed with PLy-bound discs (0.22).

The values in Table 5 demonstrate the sensitivity of the assay when tested against decreasing amounts of monoclonal antibody (moAb).

TABLE 5

ABILITY OF NITROCELLULOSE-BOUND PLy AND PAb TO DETECT DECREASING QUANTITIES OF MONOCLONAL ANTIBODY

| moAb | ng Added | Avg. OD$_{495}$ ($\pm$ s.d.)* | |
| --- | --- | --- | --- |
| | | PLy | PAb |
| GPIIb/IIIa | 500 | 1.40 (.02) | 1.02 (.01) |
| | 200 | 1.05 (.02) | 1.11 (.05) |
| | 100 | .78 (.08) | .88 (.03) |
| | 50 | .40 (.02) | .36 (.05) |
| | 20 | .35 (.01) | .40 (.01) |
| GP Ia | 20 | .45 (.02) | .41 (.01) |
| PG IIb | 20 | .33 (.02) | .38 (.01) |

*BSA control = .22 $\pm$ .05
Anti-mouse IgG = .16 $\pm$ .01

Compared to the BSA or anti-mouse IgG control values of 0.220 and 0.160, respectively, as little as 20 ng of monoclonal antibody (moAb) directed against GPIb, GPIIb, or GPIIb/IIIa could easily be detected. Optical density values of these moAb at this concentration were at least 30% greater than the controls, while 500 ng of the GPIIb/IIIa antibody were 5–7 times higher. Compared to PLy, less than an 8% loss in activity of any of the moAb was noted using the PAb discs, showing that these immunologically important surface antigens have not been lost during the absorption.

The ELISA system was tested for its ability to detect platelet antibody in the serum of two thrombocytopenic patients, alloimmunized through multiple platelet transfusions (sera AF and DP). These sera were strongly positive in a the platelet antibody screen routinely performed by the Histocompatibility Test Laboratory at M.D.A.H., both being reactive at a serum dilution greater than 1:90, as well as being cytotoxic to more than 60% of a 56-cell panel of cells in a lymphocytotoxic antibody screen.

Figure 4:
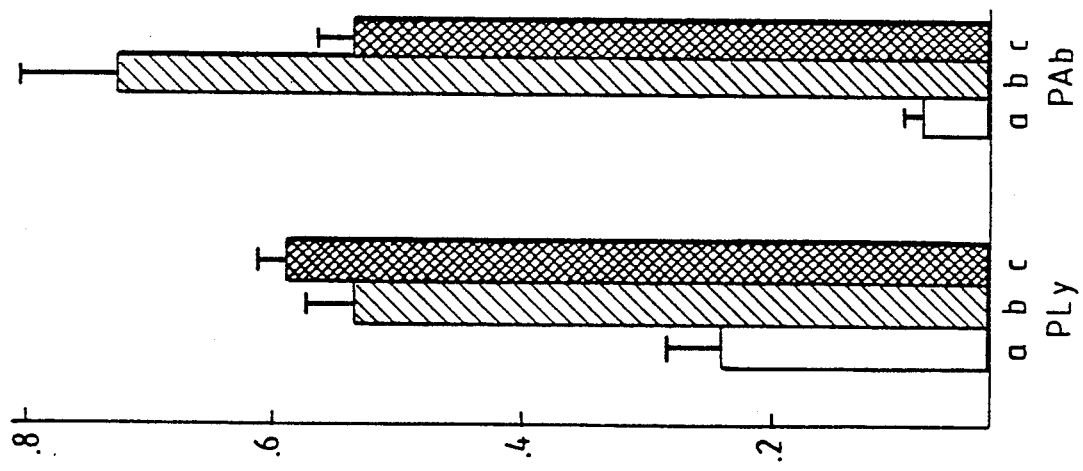
FIG. 4 shows the ability of nitrocellulose-bound PLy and PAb to detect alloantibodies in immunized patients. Nitrocellulose-bound PLy or PAb, 20 ug/ml, were prepared as described herein, and each incubated with 100 ul of a) normal serum, b) AF or c) DP, diluted 1:10 in TBS. Alkaline phosphatase-coupled anti-IgG was used to detect the bound antibody.

In FIG. 4, this strong reactivity of AF and DP with immobilized PLy was reflected by a 2.3 to 2.5-fold increase in enzyme activity above the control, respectively. However, when the same sera were used with the NC-bound PAb, AF reactivity increased to ten times the values obtained with PLy, and 23.7 times greater than the control values. Likewise, DP reactivity with PAb was shown to be 16.7 times higher than the control. The increase in reactivity of AF from 0.54 with PLy to 0.71 with PAb probably represented an increased amount of specific proteins bound to the discs following absorption of PLy with AgIgG.

Figure 5:
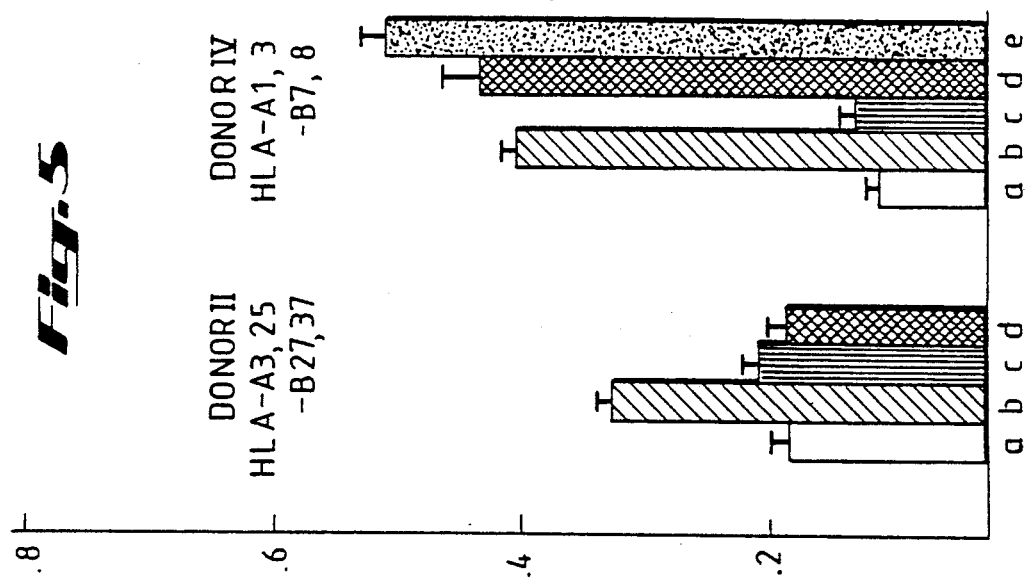
FIG. 5 shows the retention of activity of class I histocompatibility antigens in PAb. Platelet detergent lysates were prepared from two HLA-typed individuals, absorbed with AgIgG and applied to nitrocellulose discs (20 ug/disc) as described herein. Normal serum (a), antiserum to P1$^{A1}$ (b), anti-HLA-A3 (c), anti-HLA-BB (d), and anti-HLA-A1 (e), all diluted 1:10 with TBS, were used to probe for the retention of activity of these antigens in an alkaline phosphatase-coupled anti-IgG immunoassay.

The ELISA results of two different PAb using alloantisera to measure the presence of HLA-specific antigens are presented in FIG. 5. Although donor II presents HLA-A3 on his lymphocytes (see Table 2), its expression in PAb is minimal, showing a 5.3% increase in reactivity when compared to the normal serum control. As expected, no HLA-B8 could be detected. Donor IV (HLA-A1,3; B7,8) reacted strongly with antisera to both A1 and B8 with increases in reactivity of 170% and 146%, respectively, but demonstrated only a 6% increase in anti-A3 reactivity above the control.

Various quantitative assays for the measurement of platelet-associated immunoglobulin (Ig) have been developed to aid in the study of the pathophysiology of immune mediated platelet destruction. An inherent difficulty to most of these, however, has been the fact that both specific and non-specific antibody binding are indistinguishable. In fact, the contribution of the latter to the total detectable antibody is high enough to often render these test results useless. This is especially problematic since the difference between Ig concentrations on normal and antibody-sensitized platelets can be quite small. The present invention includes a method that overcomes some of these problems. A benefit of use of the present invention is an in vitro crossmatch assay that could be used to predict the outcome of platelet transfusions.

The present invention involves the use of a dialyzable nonionic detergent such as an alkyl-N-methylglucamide or alkylglycoside to solubilize human platelets for functional studies of the membrane components. Of importance in the method of the present invention is the ability to remove excess detergent through dialysis, thereby obviating problems such as those involving reconstitution and protein concentration measurements. In addition, it is known that detergent can prevent the binding of antigen by moAB and can inhibit assays that involve immunoprecipitation of antigens from detergent solutions. It has previously been shown that the plastic microwells used for some ELISA and hybridoma screening procedures are inefficient at binding protein in the presence of detergent. Although other methods have been used to remove detergents from membrane lysates, none was as simple and without as many deleterious effects on the solubilized membrane components as dialysis.

The most preferred detergent of the present invention is decanoyl-N-methyl glucamide (Mega-10). Platelets were solubilized by Mega-10 as described above, with an efficiency of about 27%, based on the dry weight of approximately $10^6$ platelets of 4 ug. This is comparable to the data presented by Kunicki et al. using 0.5% NP40 solubilized, radiolabeled platelets. Twenty micrograms of material bound to each disc, then, represents the lysate from about $1.8 \times 10^7$ platelets, which should allow for the detection of even minor components of the platelet membrane in a crude preparation of low levels of specific antibody.

One of the primary objectives of the present invention is to eliminate or reduce to an insignificant level the binding of nonimmune IgG to the platelet surface components. Previous attempts by the inventor to inhibit this "non-specific" or nonimmunospecific binding involving various standard blocking reagents including detergents, gelatin, casein, low ionic strength buffers, or with increased incubation temperatures, were unsuccessful. This led to the hypothesis that this binding was, in fact, specific although not immunospecific, with an affinity for platelet membrane component(s) strong enough to resist dissociation with the usual methods employed to reduce such IgG absorption. The results obtained following absorption of detergent solubilized platelets with agarose-bound IgG indicate that such membrane components do exist and that their removal does not alter the presence in PAb of immunologically relevant membrane antigens.

The ability of the dialyzed, Mega-10 solubilized PLy/PAb to inhibit specific, complement-mediated lymphocytotoxicity is in contrast to previous attempts by Cook et al. (Cook et al. (1985) Hum. Immunol., 14:234-244) in which NP40 present in the preparation nonspecifically inhibited cytotoxicity, and to work by the inventor with Triton X-100, the presence of which nonspecifically the cells. The fact that PLy from a donor known to possess HLA A-3 (Donor II) or B-44(12) (Donor III) did not inhibit lysis of any population of lymphocytes expressing these antigens was notable. It has long been recognized that the platelets and leukocytes from the same subject may type discrepantly for some HLA antigens. Interestingly, the PLy from donor III, whose lymphocytes contained the B-44 private epitope, did not inhibit either anti-B-12 (the public epitope) or anti-B-44 activity, whereas antisera to B-12 and the B-45 subtype were completely inhibited by PLy from Donor II, whose lymphocytes express both these antigens. This lack of inhibition could be due in part to a low level of antigen expression. This might occur if, in fact, these histocompatibility antigens are adsorbed onto the surface of platelets. Indeed the ELISA results reported here indicate that although a low level of HLA-A3 is detected, the quantity of this antigen, or perhaps its molecular conformation in the detergent lysate renders PLy/PAb incapable of absorbing anti-A3 activity under the conditions described and thus, cannot inhibit lymphocytotoxicity. Recent evidence supporting the former phenomenon has been presented by Saidman et al. (Saidman et al. (1986) in Abstracts of the Twelfth Annual Meeting for the Amer. Soc. of Histocompatibility and Immunogenetics, New Orleans, LA., p 91), who used fluorescent cell sorting analysis and monoclonal antibodies to various public and private HLA epitopes to demonstrate the varied level of expression of the antigens on platelets. This inhibition assay could prove useful for determining which HLA antigens are present on platelets in amounts sufficient to elicit an immune response or to be recognized by antibodies and fix complement. These results would provide valuable information for platelet transfusion therapy.

The fact that stored NC-immobilized PLy-PAb is stable over an extended period is of value to both research and clinical laboratories. As alluded to by Newman et al., because hundreds of discs can be made at one time, hybridoma or immune serum screening can be accomplished with both rapidity and reproducibility. Also, the immunological function of purified and immobilized membrane glycoproteins can be easily studied in this manner. Especially evident is the sensitivity of the assay when using small quantities of immobilized antigen or moAB.

It was fortuitous that two allosera with broad specific antibodies could be found to test in this ELISA. Although the reactivities of both AF and DP sera are obviously greater than that of normal sera to PLy, the use of PAb in such as assay should be a benefit in exaggerating the difference between low positive and normal serum control values.

Also relevant to clinical laboratories is the fact that moAB probes can be used to detect the level of expression of specific platelet glycoproteins using PAb prepared from patients with thrombocytopenic conditions such as Bernard-Soulier syndrome (a severe reduction of GPIb expression), or Glanzman's thrombocytopenia (a decrease in the amount of membrane associated GPIIb and GPIIIa). These as well as other still unidentified antigens are implicated as targets for platelet-directed antibodies in idiopathic, disease-associated, and alloimmune thrombocytopenias. The application of this immunoassay to routine platelet crossmatching is readily envisioned.

Serum samples will be collected from patients with clinically demonstrable refractoriness to platelet transfusions. An aliquot of the platelet rich plasma will be removed from the units selected for transfusion. The platelets will be solubilized, absorbed with agarose-bound IgG, and the PAb immobilized on the NC discs for use in the described ELISA. The predictive value of this assay as a crossmatch procedure will then be done retrospectively by monitoring the posttransfusion platelet increment and comparing it to the obtained ELISA results.

Van der Velden et al. (1986) (Br. J. Haematol., 62-635-640) have used a seemingly adaptable "Z-score" calculation to predict the transfusion outcome based on results of a $^{51}$Cr-platelet lysis assay. This Z-score is expressed as the difference between test values and transfused, nonrefractory controls relative to the standard deviation of the control values. In that study, a score of 3 or less was determined to be a negative crossmatch. Such a value, of course, would have to be determined by a laboratory seeking to quantitate successful transfusion predictabilities.

The determination of circulating antibodies to platelets has well documented importance as both adjunct and confirmative information for clinicians. This is attested to in the literature by the number and variety of platelet antibody assays attempted over the years. In the past, a simple, sensitive, and rapid assay had not been developed due especially to the inherent difficulties in working with platelets in vitro. A passive latex agglutination test (LAT) would provide such an assay not only to the pathologist in the institutional medical laboratory, but also to the physician in his private clinic or office. Although many LAT for the detection of antigen (i.e. antibody bound to the latex beads) are currently available for clinical laboratory, (for a review, see K. Hechemy and E. Michaelson 1984; Lab Med 22(6):27–40 and 22(7):26–35; L. Bangs 1984: Uniform Latex Particles, a publication of Seradyn, Inc., Indianapolis, Ind.); few products offer immobilized heterlogous antigen preparations on the beads, since the latter is biochemically a more complex problem. The present invention provides a method whereby serum may be tested for antibodies directed against platelet antigens using such a rapid latex agglutination test. The ease of performance, sensitivity, and speed of these assays make them valuable diagnostic tools for the clinician.

The following methods describe the attachment of the aforementioned partially purified platelet antigens, PAb, to polystyrene latex particles (LP) of variable sizes, and the use of the coated particles in a rapid latex agglutination test for the detection of anti-platelet antibodies. Optional discrimination between antibodies directed against certain integral platelet membrane proteins and antibodies directed toward antigens adsorbed to the platelet membrane (for example, certain HLA antigens) is made possible with the inclusion of an additional purification step. Of course, any antigen associated with the platelet surface is considered to be a platelet antigen for purposes of the present invention.

Reagents used in development of a prototypical assay procedure were as follows: pooled human AB serum (NS) was purchased from Irvine Scientific (Irvine, Calif.). Anti-PL$^{A1}$ and anti-HLA sera were supplied as previously detailed. Additional multi-specific anti-HLA serum was obtained from GenTrak, Inc. (Wayne, Pa.). Rabbit anti-human thrombocyte serum was supplied by DAKO, Inc. (Santa Barbara, Calif.). Frozen lymphocyte panels were purchased from Pel Freeze (Brown Deer, Wis.). Patient sera were collected from the M.D. Anderson Hospital and Tumor Institute Blood bank. These patients were referred to the laboratory for routine anti-platelet antibody tests, performed during using a modification of the immunoperoxidase assay previously described. (Trinidad, et al., in Abstracts of the Ninth Annual Meeting of the American Association of Clinical Histocompatibility Testing, Chicago, Ill., p. 50 (1983).) When positive, these sera were tested for the presence and specificity of lymphocytotoxic antibodies (HLA specific antibodies) using a panel of frozen lymphocytes with defined HLA antigen types.

PAb was prepared as described above, and dialyzed for 16-24 hours against 100 mM glycine-buffered saline, pH 8.2, 0.02% sodium azide (GBS). HLA-free PAb (PAb-HF) was prepared by treating pooled platelets for 90 min. at 4° C. with chloroquine diphosphate (Gamma Biologicals, Houston, Tex.), 200 mg/ml in 100 mM phosphate-buffered saline, 1 mM EDTA, pH 5.0, at 4:1 (v/v), as described by Blumberg et al. (Blood, 1984, 63:448–450). Alternatively, HLA-free PAb could be prepared by absorbing the PAb with either agarose-bound antibody to the beta$_2$-microglobulin subunits of the HLA Class I molecule, or antibody from the W6/32 cell line, which recognizes a monomorphic epitope on the heavy chain of human HLA-A,-B,-C antigens (C. J. Barnzstable et al., Cell, 1978, 14:9). Both of these antibodies are commercially available. The chloroquine-treated platelets were washed twice with 50 mM TBS, pH 7.6, before the described detergent solubilization and agarose-IgG absorbtion. Protein concentrations were determined before and after all absorptions.

The PAb were then affixed to latex particles by passive adsorption. Although other techniques such as forced absorption or covalent coupling could be used to coat the LP with PAb, the following procedure was successfully employed.

Polystyrene, monodispersed latex particles (LP) (Polysciences, Inc., Warrington, Pa.) were washed four times with GBS and resuspended at a 2.5% solution in GBS. LP of various sizes between 0.1 to 1.5 microns in diameter have all been successfully used. Various amounts of PAb or PAb-HF were added to 100 ul of LP, and the reactants were mixed on a rotator for 15 min. at room temperature. To determine the ratio of free (FAg) to bound (BAg antigen), a 60 ul aliquot was removed and centrifuged at 10,000 X g for 10 min. The supernate of this aliquot was removed and assayed for protein concentration. (Hechemy, et al., *J. Clin Microbiol.*, 4:82–86 (1976).) The amount of antigen bound to the latex was then calculated by subtracting the total free antigen from the quantity of antigen added to the latex mixture.

TABLE 6
PREPARATION OF STABLE PAb-COATED LATEX PARTICLES

| Sample | ug PAb Added | ug Free PAb | ug Bound PAb* | FAg:BAg |
|---|---|---|---|---|
| 1 | 50 | 8 | 42 | 0.19 |
| 2 | 100 | 7 | 93 | 0.08 |
| 3 | 150 | 56 | 94 | 0.60 |
| 4 | 200 | 83 | 117 | 0.71 |
| 5 | 300 | 165 | 135 | 1.20 |
| 6 | 500 | 309 | 191 | 1.62 |

*calculated. i.e., ug PAb added − ug free PAb.

Present experience indicates that determinations of a FAg:BAg ratio may be quite important for the ultimate success of the latex agglutination assay. A latex suspension to which inadequate amounts of protein have been added will be unstable and the LP will tend to aggregate spontaneously. Furthermore, the amount of protein that must be added in order to produce a stable suspension will vary with the size of the particle employed. Therefore, when one desires to use a smaller or larger particle, it will usually be necessary to prepare a saturation curve to determine the amount of antigen which must be added to the particle suspension to effect a given FAg:BAg.

Table 6 illustrates FAg:BAg ratios found using 1.0 micron latex particles. In additional experiments, antigen concentrations were varied to effect FAg:BAg ratios of from 1.6 to 6.0. While particles having a FAg:BAg less than about 1.6 were unstable and tended to clump spontaneously, LP particles having FAG:BAg between about 1.6 and about 6.0 were found to be stable and still sensitive to agglutination by specific antibodies. Therefore, for purposes of the present invention, it is preferred that the coated latex particle suspension have a FAg:BAg ratio close to or within this range. The following experiments were performed with latex suspensions having FAg:BAg ratios from about 1.6 to 2.3.

After determination of FAg:BAg, the volume of the coated LP suspension was adjusted to 500 ul with GBS, and 5 ul of 10% BSA (fatty-acid and globulin free) was added to the latex solution as a stabilizer prior to storage at 4° C.

For the latex agglutination assay, 50 ul of coated LP was mixed with 50 ul of GBS in a 10×75 mm glass test tube. Fifty microliters of test serum was added, and the tube placed on a mechanical rotator at 160 rpm for 10 min. The tubes were inspected macroscopically for agglutination, and rated as 4+ (clear supernate, large LP clumps), 2+ (noticeable clumps, but milky supernate), 0 (no agglutination, no visible difference from normal serum control). Generally speaking, a 4+ rating indicated a relatively high or intermediate level of antibody, a 2+ rating indicated a low level of antibody, and a 0 indicated that antibody was undetectable. Table 7 summarizes the agglutination reactions of PAb/PAb-HF coated 0.5 micron LP (FAg:BAg=2.0) with various test sera.

TABLE 7
COMPARISON OF ASSAYS FOR PLATELET ANTIBODIES[a]

| ANTISERUM[b] | PAb | PAb-HF | PLATELET Ab IPA | CYTO-Ab ASSAY | ANTI-HLA SPECIFICATIONS |
|---|---|---|---|---|---|
| NS (20) | 0[c] | 0 | 0 | 0 | |
| PL[Al] (20) | + | + | + | NT | |
| Thrombocyte (50) | + | + | + | NT | |
| HLA (4) | + | 0 | + | + | B-8,12 |
| HLA pool (6) | + | 0 | + | + | multiple |
| Patient Sera | | | | | |
| 1. L J | 0 | 0 | 0 | NT | |
| 2. S R | 0 | 0 | 0 | NT | |
| 3. H P | 0 | 0 | 0 | NT | |
| 4. N S | 0 | 0 | 0 | NT | |
| 5. A I | 0 | 0 | 0 | NT | |
| 6. T H | 0 | 0 | 0 | NT | |
| 7. B W | 0 | 0 | 0 | NT | |
| 8. D O | 0 | 0 | 0 | NT | |
| 9. R D | + | 0 | + | + | A-11 |
| 10. D F | + | 0 | + | + | A-9 |
| 11. J E | + | 0 | + | ± | nonspecific |
| 12. A T | + | 0 | + | + | A-1,25<br>B-8,18,35,62 |
| 13. V W | + | 0 | + | + | A-2,9 |
| 14. R E | + | + | + | 0 | |
| 15. G R | ± | ± | 0 | 0 | |

TABLE 7-continued

COMPARISON OF ASSAYS FOR PLATELET ANTIBODIES[a]

| ANTISERUM[b] | PAb | PAb-HF | PLATELET Ab IPA | CYTO-Ab ASSAY | ANTI-HLA SPECIFICATIONS |
|---|---|---|---|---|---|
| 16. L S | + | ± | — | 0 | |

[a]Abbreviations:
PAb and PAb-HF: latex particles coated with respective prepared platelet reagent.
Platelet Ab IPA: immunoperoxidase platelet antibody test.
Cyto Ab Assay: lymphocytotoxic antibody assay.
[b]Number in parenthesis is the inverse of the working dilution; all patient sera tested undilute.
[c]0 = no agglutination.
+ = 4+ agglutination.
± = 2+ agglutination on latex; < 30% cytotoxicity in Cyto Ab assay.
NT = not tested.

From this data, it can be seen that anti-Pl[41], anti-thrombocyte, and the anti-HLA allosera all showed 4+ agglutination against both LP preparations when tested at the concentrations indicated. Agglutination was complete within ten minutes. Two-fold dilutions of normal serum were tested against coated LP to insure that lack of agglutination was not a prozone-like phenomenon. These dilutions never agglutinated the LP coated with either PAb or PAb-HF, even when examined after 24 hr. incubation.

In addition, Table 7 shows a comparison of the latex agglutination assay of the present invention with the immunoperoxidase assay (IPA), currently used in the laboratory of the present inventors (Trinidad, et al., in Abstracts of the Ninth Annual Meeting of the American Association of Clinical Histocompatibility Testing, Chicago, Ill., p. 50 (1983).) All patient sera positive by immunoperoxidase assay (IPA) agglutinated PAb-coated LP, while all but one (#15) of the IPA-negative sera consistently failed to agglutinate the latex beads. Anti-HLA alloantisera and serum from patients #9-13 agglutinated PAb-LP. However, these IPA positive, lymphocytotoxic antibody positive sera were negative using PAb-HF, indicating that the antibodies in these samples were directed against HLA determinants found on the platelet surface and that these HLA antigens could be successfully removed with the chloroquine treatment. Anti-Pl[41] and anti-thrombocyte agglutinated both PAb and PAb-HF equally well, demonstrating the stability and immunologic reactivity of the PAb-HF with anti-platelet antiserum.

Serum from patient #14 was IPA positive, but negative in the cytotoxic antibody screen. This patient had been transfused with >150 units of platelets during the course of his hospitalization. Interestingly, his serum agglutinated both PAb and PAb-HF LP and appears to contain antibodies to non-HLA antigens (Pl[41], GP Ib, etc.) or the platelet surface.

Sera #15 and #16 were both from patients with lymphoma, a malignancy of immunoglobulin-secreting B lymphocytes who had received or were receiving interferon therapy at the time of platelet antibody testing. These patients had normal platelet counts and no evidence of alloimmunization. Both sera showed noticeable (2+ or 4+) agglutination of both PAb and PAb-HF LP. While #15 was IPA negative and #16 was IPA positive, neither had cytotoxic antibodies. Since the IPA assay uses enzyme-labeled anti-IgG, it is possible that the agglutination observed with sample #15 was mediated by an IgM antibody produced by the malignant cells. It is doubtful that the detected antibody in the serum of patent #16 was directed against any platelet surface antigen since no immune destruction of the platelets was evident. Although the presence of immune complexes in the serum that could bind to the platelet membrane cannot be ruled out (tests not performed), the exact nature of the immunoglobulins from lymphoma patients requires further characterization.

An important advantage of the latex assay provided by the present invention is the speed, only 10-15 min. required for completion. In contrast, the IPA assay requires approximately three hours to perform. To date, the PAb/PAb-HF-coated LP have been stored at 4° C. for 75 days with no apparent decrease in reactivity. Continuing stability studies are in progress. PAb-HF appears particularly valuable in distinguishing the specificity of platelet directed antibodies. Such information would be of value for the transfusion therapist, aiding in the selection of the most suitable donors for alloimmunized patients.

In conclusion, the present invention comprises a procedure by which platelet crossmatching reagents can be easily prepared for use in a semiquantitative immunoassay or rapid latex agglutination assays. Long term storage of these reagents makes it possible to screen a large donor pool and select donors compatible with a patient prior to harvesting platelets from any of the selected individuals. The invention also provides an optional modification allowing discrimination between HLA antibodies and certain other antiplatelet antibodies.

Changes may be made in the construction, operation and arrangement of the various parts, elements, steps and procedures described herein without departing from the concept and scope of the invention as defined in the following claims.

What is claimed is:

1. A method for detecting human antibodies in a biological sample directed against platelets, the method comprising the steps of:
  treating platelets with an aqueous solution comprising a dialyzable nonionic detergent to solubilize platelet antigens comprising HLA and platelet specific antigens and to produce a detergent lysate;
  separating insoluble material and excess detergent from the detergent lysate so as to minimize interference with subsequent binding of antibodies directed against platelet antigens to platelet antigens and to produce a detergent-free lysate;
  removing from the detergent-free lysate substances nonimmunospecifically binding to human IgG by passing the lysate over a column of matrix-bound human IgG to produce partially purified platelet antigens;
  affixing the partially purified platelet antigens to a particulate solid matrix to produce an antigen-coated particulate latex matrix wherein the platelet antigens are passively coated onto the latex particles to achieve a ratio (weight/weight) of unaffixed antigen to affixed antigen of from about 1.6 to about 6.0;

contacting said antigen-coated particulate latex matrix with a solution comprising a human biological sample possibly containing antibodies directed against platelets under conditions appropriate for formation of immunocomplexes; and detecting agglutination of antigen-coated particulate latex matrix; said agglutination resulting from formation of immunocomplexes between the matrix-bound antigen and antibodies of the biological sample directed against platelets.

2. A method for detecting antibodies in a biological sample directed against platelets, the method comprising the steps of:

obtaining a blood sample and isolating a platelet sample therefrom;

eluting HLA antigens from the platelet sample by treating the platelet sample with chloroquine to produce essentially HLA-free platelets;

treating the essentially HLA-free platelets with an aqueous solution comprising a dialyzable nonionic detergent to solubilize the platelet antigens comprising platelet-specific antigens and to produce a detergent lysate;

separating insoluble material and excess detergent from the detergent lysate to minimize interference with binding of antibodies directed against platelet antigens to platelet antigens and to produce a detergent-free lysate;

removing from the detergent-free lysate substances nonimmunospecifically binding to human IgG by passing the lysate over a column of matrix-bound human IgG to produce partially purified platelet antigens;

affixing the partially purified platelet antigens to a particulate solid latex matrix wherein the platelet antigens are passively coated onto the latex particles to achieve a ratio (weight/weight) of unaffixed antigen to affixed antigen of from about 1.6 to about 6.0;

contacting said latex matrix with a solution comprising the biological sample possibly containing antibodies directed against platelets under conditions appropriate for formation of immunocomplexes; and detecting agglutination of matrix latex particles, said agglutination resulting from formation of immunocomplexes between the matrix-bound antigen and antibodies of the biological sample directed against platelets.

3. A method for detecting antibodies in a human biological sample directed against human platelets, the method comprising the steps of:

obtaining a human blood sample and isolating human platelets therefrom;

treating the human platelets with an aqueous solution comprising a dialyzable nonionic detergent to solubilize platelet antigens comprising HLA antigens and platelet-specific antigens and to produce a detergent lysate;

separating insoluble material and excess detergent from the detergent lysate to minimize interference with binding of antibodies directed against human platelet antigens to platelet antigens and to produce a detergent-free lysate;

contacting the detergent-free lysate with HLA-reactive antibodies attached to a solid matrix to produce an essentially HLA-free platelet lysate;

removing from the essentially HLA-free platelet detergent-free lysate substances nonimmunospecifically binding to human IgG to produce partially purified human platelet antigens;

affixing a fraction of the partially purified human platelet antigens to a particulate latex matrix to produce a suspension having a ratio (weight/weight) of human unaffixed antigen to human affixed antigen from about 1.6 to about 6.0, and wherein the platelet antigens are passively coated onto the latex particles;

mixing with said suspension a solution comprising a human biological sample possibly containing antibodies directed against platelets under conditions appropriate for formation of immunocomplexes; and detecting agglutination of latex matrix particles; said agglutination resulting from formation of immunocomplexes between the latex matrix-bound human antigen and human antibodies of the biological sample directed against platelets.

4. The method of claim 1 comprising the additional step of eluting HLA antigens from the platelet surface by chloroquine treatment prior to the treating step.

5. The method of claim 1, 2 or 3 wherein the detergent is an alkyl-N-methylglucamide or an alkylglycoside.

6. The method of claim 1, 2 or 3 wherein the detergent is an alkyl-N-methylglucamide.

7. The method of claim 1, 2 or 3 wherein the detergent is decanoyl-N-methylglucamide, nonanoyl-N-methylglucamide, octanoyl-N-methylglucamide or heptanoyl-N-methylglucamide.

8. The method of claim 1, 2 or 3 wherein the detergent is decanoyl-N-methylglucamide.

9. The method of claim 1, 2 or 3 wherein the detergent is n-decyl beta-D-glucopyranoside, n-dodecyl beta-D-glucopyranoside, n-dodecyl beta-D-maltoside, n-heptyl beta-D-glucopyranoside, n-hexyl beta-D-glucopyranoside, n-octyl beta-D-glucopyranoside, n-nonyl beta-D-glucopyranoside or n-octyl alpha-D-glucopyranoside.

10. The method of claim 1, 2 or 3 wherein the aqueous solution comprises between about 0.2% and about 0.5% dialyzable nonionic detergent.

11. The method of claim 1, 2 or 3 wherein the insoluble matter is separated by a step comprising centrifugation.

12. The method of claim 1, 2 or 3 wherein the excess detergent is separated by a step comprising dialysis.

13. The method of claim 3, wherein the removal of substances nonimmunospecific binding to human IgG comprises contacting the solution with human IgG attached to a solid matrix.

14. The method of claim 3, wherein the HLA-reactive antibodies are attached to an agarose solid matrix.

15. The method of claims 1, 2 or 3, wherein the particulate latex matrix comprises latex beads.

16. The method of claim 3 wherein separating excess dialyzable nonionic detergent comprises;

dialyzing the detergent lysate to produce a detergent-free lysate; and wherein separating insoluble material comprises centrifugation of the lysate.

17. A composition of matter comprising latex particles having partially purified platelet antigens affixed thereto, said particles suspended in a solution having soluble partially purified platelet specific antigens dissolved therein wherein the ratio of (weight/weight) of soluble antigen to affixed antigen is about 1.6 to 6.0, and wherein said platelet antigens are passively coated onto the latex particles.

* * * * *